United States Patent
Cheong et al.

(10) Patent No.: US 8,057,751 B2
(45) Date of Patent: Nov. 15, 2011

(54) STERILIZING APPARATUS AND METHOD USING HIGH PRESSURE STEAM

(75) Inventors: Yeon-Seong Cheong, Busan (KR); Soo-Beom Son, Busan (KR)

(73) Assignee: Aqua Doctor Co., Ltd., Jangnim-dong, Saha-gu, Busan (KR)

( * ) Notice: Subject to any disclaimer, the term of this patent is extended or adjusted under 35 U.S.C. 154(b) by 677 days.

(21) Appl. No.: 12/065,319

(22) PCT Filed: Aug. 31, 2006

(86) PCT No.: PCT/KR2006/003465
§ 371 (c)(1), (2), (4) Date: Feb. 29, 2008

(87) PCT Pub. No.: WO2007/027067
PCT Pub. Date: Mar. 8, 2007

(65) Prior Publication Data
US 2008/0233004 A1    Sep. 25, 2008

(30) Foreign Application Priority Data
Sep. 1, 2005    (KR) .................. 10-2005-0081427

(51) Int. Cl.
*A61L 2/00* (2006.01)
*A61L 9/00* (2006.01)
*A61L 2/08* (2006.01)

(52) U.S. Cl. ........................... 422/292; 422/26

(58) Field of Classification Search .................. 422/292, 422/293; 239/383, 214.13, 214.19, 154; 261/88

See application file for complete search history.

(56) References Cited

U.S. PATENT DOCUMENTS

| 3,633,829 | A | * | 1/1972 | Adams ........................... 239/428 |
| 4,821,961 | A | * | 4/1989 | Shook ........................... 239/253 |
| 5,020,556 | A | * | 6/1991 | Lamminen et al. ........... 134/112 |
| 5,685,487 | A | * | 11/1997 | Ellis ............................ 239/261 |
| 6,585,934 | B1 | | 7/2003 | Oberleitner et al. |

FOREIGN PATENT DOCUMENTS

EP    1 516 632 A1    3/2005
(Continued)

OTHER PUBLICATIONS

Search Report issued in International Application No. PCT/KR2006/003465 on Dec. 11, 2006.

*Primary Examiner* — Sean E Conley
*Assistant Examiner* — Regina Yoo
(74) *Attorney, Agent, or Firm* — Stein McEwen, LLP (57) ABSTRACT

A sterilizing apparatus is inserted into a cold or warm water passage of a water dispenser, a purified water passage of a water purifier, a discharge pipe of a beverage bending machine, an air suction unit of an air conditioner and so on to inject a high pressure steam for sterilization. The sterilizing apparatus using a high pressure steam includes an injection member for controlling a high pressure steam to be selectively injected; a rotating unit having a hollow perforated in a length direction of the rotating unit so that the steam injected from the injection member passes through the hollow, a rotating means being installed in the hollow to be rotated by the passing steam; and a nozzle unit coupled to the rotating means to rotate together with the rotating means, and having a rod-shaped nozzle for injecting the steam.

4 Claims, 8 Drawing Sheets

FOREIGN PATENT DOCUMENTS

| | | |
|---|---|---|
| JP | H7-60165 | 3/1995 |
| JP | 2000-237088 | 9/2000 |
| JP | 2000-325895 | 11/2000 |
| JP | 2001-179199 | 7/2001 |
| JP | 2002-22393 | 1/2002 |
| KR | 2003-91128 | 12/2003 |

* cited by examiner

STERILIZING APPARATUS AND METHOD USING HIGH PRESSURE STEAM

CROSS-REFERENCE TO RELATED APPLICATIONS

This application claims the benefit of PCT International Patent Application No. PCT/KR2006/003465, filed Aug. 31, 2006, and Korean Patent Application No. 2005-81427 filed Sep. 1, 2005, in the Korean Intellectual Property Office, the disclosures of which are incorporated herein by reference.

BACKGROUND OF THE INVENTION

1. Field of the Invention

The present invention relates to sterilizing apparatus and method using high pressure steam, and more particularly to a sterilizing apparatus inserted into a cold or warm water passage of a water dispenser, a purified water passage of a water purifier, a discharge pipe of a beverage bending machine, an air suction unit of an air conditioner and so on to inject a high pressure steam for sterilization, and a sterilizing method using the apparatus.

2. Description of the Related Art

Generally, a water dispenser supplies water to a user after heating or cooling the water contained in a spring water barrel to a predetermined temperature, and a water purifier purifies a tap water and then supplies the purified water to a user after cooling or heating it to a predetermined temperature. In addition, a beverage bending machine makes a coffee or the like by mixing coffee powder and sugar into water and then supplies the coffee to a user. Also, an air conditioner cools air to a predetermined temperature by passing an indoor air through an evaporator.

Figure 1:
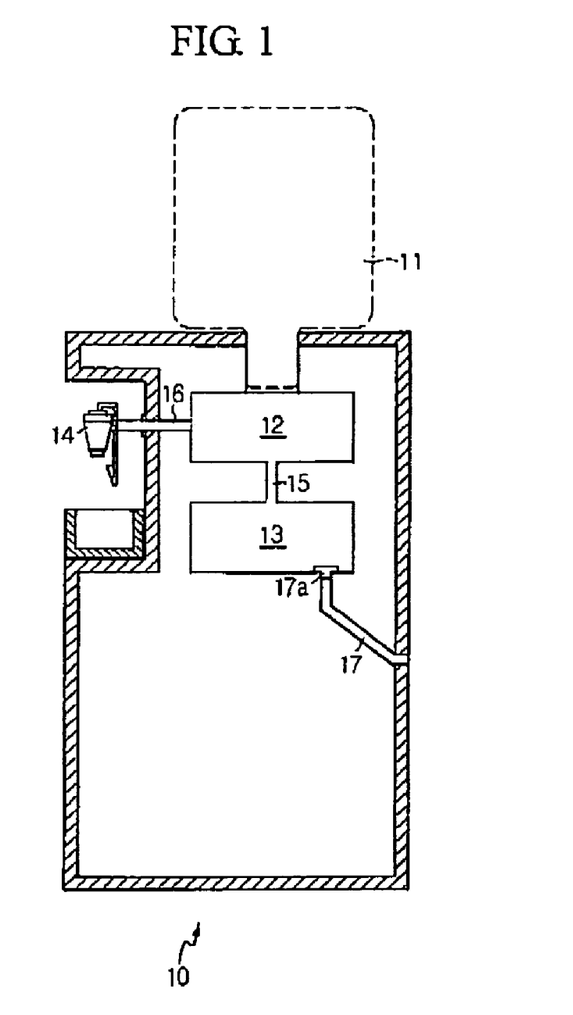
FIG. 1 is a side sectional view schematically showing a general water dispenser.

As shown in FIG. 1, the water dispenser includes a cold water container 12 for receiving and storing a spring water from a spring water barrel 11, a warm water container 13 for heating the spring water supplied from the cold water container 12 and then supplying the heated water, a cold water valve 14 for selectively drawing out the water supplied from the cold water container 12, and a warm water valve (not shown) for selectively drawing out the water supplied from the warm water container 13. The cold water container 12 is cooled by a coolant supplied from a cooling unit (not shown), and the warm water container is heated by a predetermined heater (not shown).

The water stored in the cold water container 12 is moved to the warm water container 13 through a connection pipe 15. In addition, the water stored in the cold water container 12 is moved to the cold water valve 14 through a cold water pipe 16, and the water stored in the warm water container 13 is moved to the warm water valve through a warm water pipe (not shown). In case of sterilizing or washing the water dispenser, a discharge cork is opened to discharge the water in the water dispenser 10 outward through a discharge pipe 17.

Meanwhile, the inside of the water dispenser 10 is kept at a certain temperature by the heat generated from an evaporator (not shown) of the cooling unit or the heater, which is suitable for habitation of bacteria and virus. Thus, a user should sterilize or clean the water dispenser 10 periodically. In particular, the cold water container 12, the connection pipe 15, the warm water container 13, the cold water pipe 16, the warm water pipe and the discharge pipe 17 are a passage of cold or warm water and thus easily contaminated by bacteria, virus or dust, but it is not easy to sterilize their insides. In the specification, the term 'passage of warm or cold water' is defined to include the passage through which cold or warm water passes, including the cold water container 12, the connection pipe 15, the warm water container 13, the cold water pipe 16, the warm water pipe and the discharge pipe 17.

Figure 2:
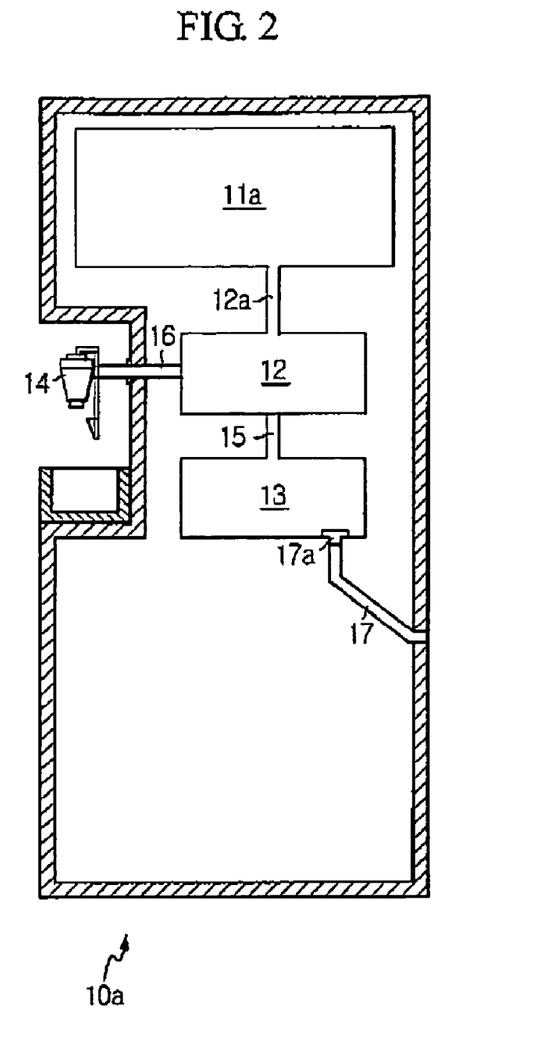
FIG. 2 is a side sectional view schematically showing a general water purifier.

As shown in FIG. 2, a water purifier 10a includes a purified water supplier 11a for purifying a tap water and storing a purified water, a cold water container 12 for cooling the water supplied from the purified water supplier 11a to a predetermined temperature and then storing the cold water, a warm water container 13 for heating the water supplied from the cold water container 12 to a predetermined temperature, a cold water valve 14 for selectively drawing out the water supplied from the cold water supplier 12, and a warm water valve (not shown) for selectively drawing out the water supplied from the warm water container 13. The cold water container 12 is cooled by a coolant supplied from a cooling unit (not shown), and the warm water container 13 is heated by a predetermined heater (not shown).

In addition, the water in the purified water supplier 11a is moved to the cold water container 12 through a supply pipe 12a, and the water in the cold water supplier 12 is moved to the warm water container 13 through a connection pipe 15. The water stored in the cold water container 13 is moved to the cold water valve 14 through a cold water pipe 16, and the water stored in the warm water container 13 is moved to a warm water valve (not shown) through a warm water pipe (not shown). In case of sterilizing or cleaning the water purifier 10a, a discharge cork 17a is opened to discharge the water in the water purifier outward.

Meanwhile, the inside of the water purifier 10a is kept at a certain temperature by the heat generated from an evaporator (not shown) of the cooling unit or the heater, which is suitable for habitation of bacteria and virus, similarly to the inside of the water dispenser 10. Thus, a user should sterilize or clean the water purifier 10a periodically. In particular, the purified water supplier 11a, the supply pipe 12a, the cold water container 12, the connection pipe 15, the warm water container 13, the cold water pipe 16, the warm water pipe and the discharge pipe 17 are a passage of cold or warm water and thus easily contaminated by bacteria, virus or dust, but it is not easy to sterilize their insides. In the specification, the term 'passage of purified water' is defined to include the passage through which the purified water passes, including the purified water supplier 11a, the supply pipe 12a, the cold water container 12, the connection pipe 15, the warm water container 13, the cold water pipe 16, the warm water pipe and the discharge pipe 17.

Figure 3:
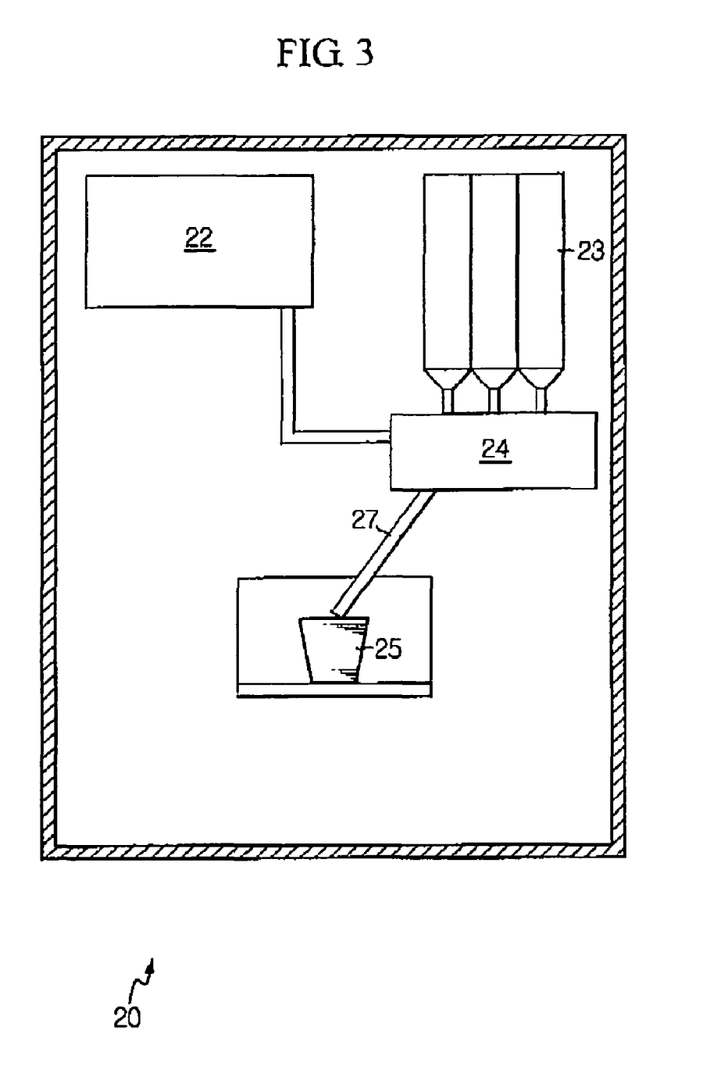
FIG. 3 is a front sectional view schematically showing a general beverage bending machine.

As shown in FIG. 3, the beverage bending machine includes a water supplier 22, a material supplier 23 for supplying coffee powder, sugar and so on, a mixer 24 for mixing coffee powder and sugar with water, and a discharge pipe 27 for discharging a mixed liquid to a cup 25.

Among the components of the beverage bending machine 20, the discharge pipe 27 is exposed to outside and allows the mixed liquid to pass through it, so bacteria and virus may easily inhabit therein. However, the discharge pipe 27 is not easy to sterilize since its side is very narrow and long.

Figure 4:
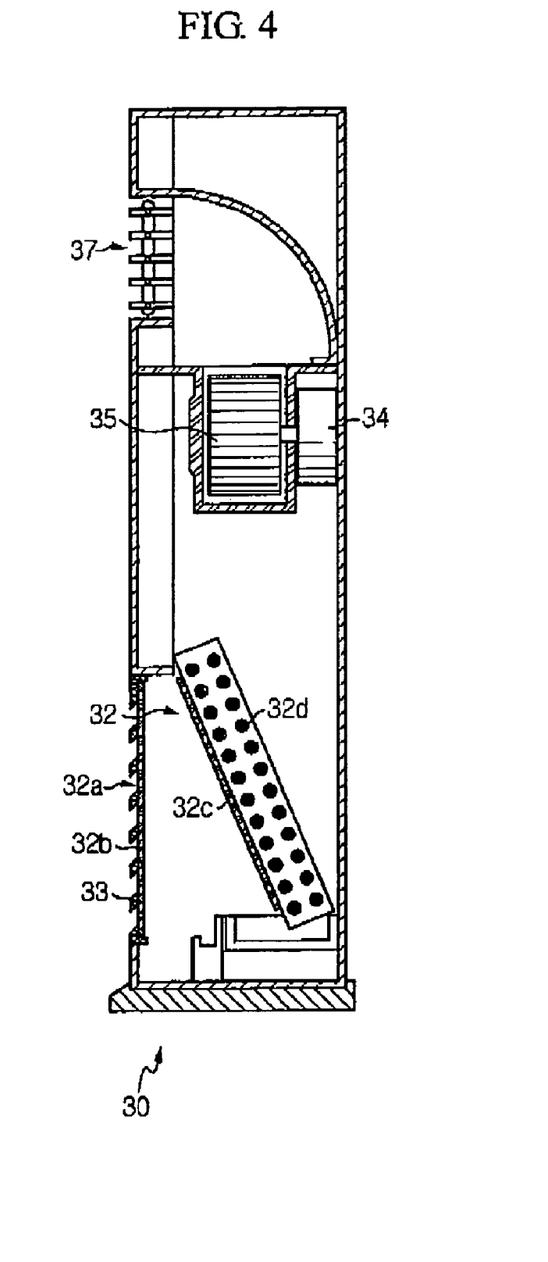
FIG. 4 is a side sectional view schematically showing a general air conditioner.

As shown in FIG. 4, the air conditioner includes an air suction unit 32 for sucking in and cooling an external air, a blowing fan 35 for moving a cooled air upward, and an exhaust unit 37 for supplying the upwardly moved air to outside. Among the components of the air conditioner, the air suction unit 32 includes filters 32b, 32c for primarily purifying the air introduced through a suction hole 32a, and an evaporation pipe 32d provided therein for a coolant to pass through it. The air suction unit 32 sucks in an external air through the filters 32b, 32c, and then passes the sucked air among the evaporation pipe 32d to cool the external air to a predetermined temperature. In this embodiment, the term 'air suction unit' is defined as a portion of an air condition, which sucks in an external air and the cools it. Meanwhile, the reference numeral 33 indicates a suction louver installed to the suction hole 32a, and the reference numeral 34 is a driving motor for operating the blowing fan 35.

As mentioned above, impurities such as dust is removed when an external air passes through the filters 32b, 32c, and the external air is cooled to a predetermined temperature with passing among the evaporation pipe 32d. Thus, many impurities may be stuck to the filters 32b, 32c and among the evaporation pipe 32d, and various virus and bacteria may easily inhibit therein. However, the evaporation 32b and the filters 32b, 32c are not easily cleaned since they have complicated structure and narrow spaces.

SUMMARY OF THE INVENTION

The present invention is designed in consideration of the above problems, and therefore it is an object of the invention to provide an apparatus inserted into a cold or warm water passage of a water dispenser, a purified water passage of a water purifier, a discharge pipe of a beverage bending machine, an air suction unit of an air conditioner and so on to inject a high pressure steam for sterilization, and a sterilizing method using the apparatus.

In order to accomplish the above object, the present invention provides a sterilizing apparatus using a high pressure steam, which includes an injection member for controlling a high pressure steam to be selectively injected; a rotating unit having a hollow perforated in a length direction of the rotating unit so that the steam injected from the injection member passes through the hollow, a rotating means being installed in the hollow to be rotated by the passing steam; and a nozzle unit coupled to the rotating means to rotate together with the rotating means, and having a rod-shaped nozzle for injecting the steam.

Preferably, a screw line of a predetermined pitch is formed in an inner surface of the hollow so that the moving steam is rotated, and the rotating means includes a cylindrical rotator having a first inflow hole formed in an outer surface thereof for introducing the steam, and a first through hole communicated with the first inflow hole and formed in a length direction thereof; and a rotary shaft integrally formed with the rotator and having a second through hole communicated with the first through hole and perforated in a length direction thereof, the rotary shaft being coupled with the nozzle unit, whereby the rotating means is rotated as the steam rotated by the screw line is introduced into the first inflow hole.

Preferably, the rotating means includes a rotary shaft having a second inflow hole formed in a side thereof for introducing the steam, and a third though hole communicated with the second inflow hole and formed in a length direction thereof for allowing the steam to be moved to the nozzle unit, the nozzle unit being coupled to an end of the rotary shaft; and a propeller installed to the other end of the rotary shaft and rotated by the moving steam.

Here, the sterilizing apparatus may further include a diffusion means installed in front of the rotating means to diffuse the steam introduced from the injection member so that the steam is closely adhered to the inner surface of the hollow.

In addition, a brush member is preferably installed to the nozzle.

Also, the nozzle is preferably elongated in a length direction so that the nozzle is injected into any of a passage of cold or warm water in a water dispenser, a passage of purified water in a water purifier, a discharge pipe of a beverage bending machine and an air suction unit of an air conditioner and then injects a steam with rotating.

In another aspect of the present invention, there is provided a sterilizing method using a high pressure steam, which includes (a) inserting a rod-shaped nozzle into any of a passage of cold or warm water in a water dispenser, a passage of purified water in a water purifier, a discharge pipe of a beverage bending machine and an air suction unit of an air conditioner; and (b) supplying a high pressure steam using an injection member so as to inject the steam through the nozzle for sterilizing.

Preferably, in the step (b), a rotating unit including a rotating means rotated by the steam is installed between the injection member and the nozzle, and the nozzle injects the steam with rotating together with the rotating means.

Preferably, the nozzle is formed to have a predetermined curvature.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 5:
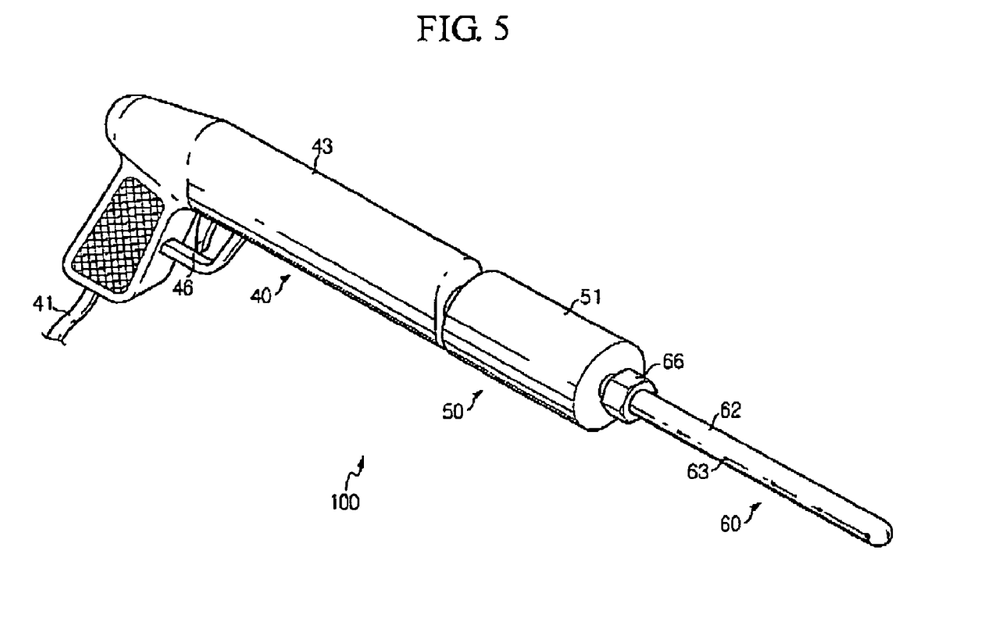
FIG. 5 is a perspective view showing a sterilizing apparatus using a high pressure steam according to a preferred embodiment of the present invention.
Figure 6:
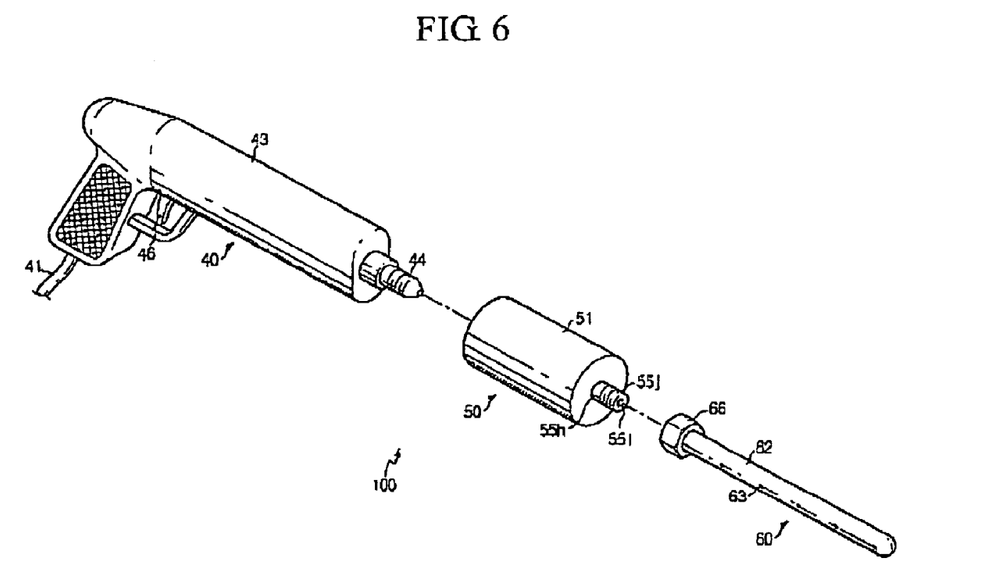
FIG. 6 is an exploded perspective view showing the sterilizing apparatus of FIG. 5.
Figure 7:
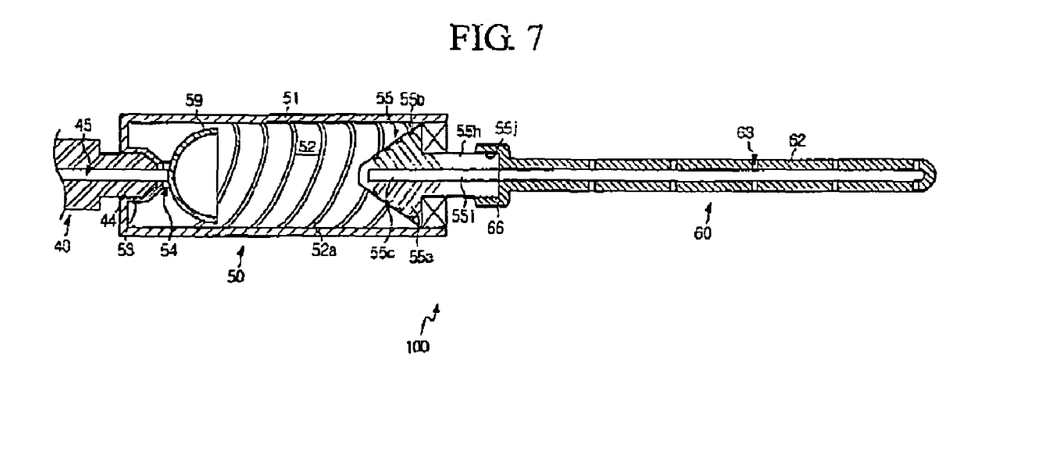
FIG. 7 is a sectional view showing a rotating unit and a nozzle unit of the sterilizing apparatus of FIG. 5.

FIG. 5 is a perspective view showing a sterilizing apparatus using a high pressure steam according to a preferred embodiment of the present invention, FIG. 6 is an exploded perspective view showing the sterilizing apparatus, and FIG. 7 is a sectional view showing a rotating unit and a nozzle unit of the sterilizing apparatus.

Referring to FIGS. 5 to 7, the sterilizing apparatus 100 includes an injection member 40 for injecting a high pressure steam, a rotating unit 50 having a rotating means 55 rotated by the steam injected from the injection member 40, and a nozzle unit 60 connected to the rotating means 55 to inject a steam with rotating together with the rotating means 55.

The injection member 40 may control a high pressure steam to be selectively injected. The injection member 40 includes a body 43 connected to a steam hose 41, a steam passage 45 formed in the body 43 to allow movement of the steam, and a controller 46 for selectively controlling injection of the steam. A screw thread 44 is formed at a front end of the body 43 for coupling with the rotating unit 50. The injection member 40 is widely used for high pressure injection of fluid, and not described in detail here. Preferably, the steam has a pressure of about 4 to 5 bars.

The rotating unit 50 includes a frame 51 having a hollow 52 perforated therein in a length direction, and a rotating means 55 installed in the hollow 52.

The frame 51 is coupled with the front end of the body 43. For this purpose, a screw thread 53 to be engaged with the screw thread 44 of the body 43 is formed at an inflow hole 54 of the frame 51. The steam injected from the injection member 40 is introduced through the inflow hole 54, moved through the hollow 52, and then discharged to the nozzle unit 60.

Preferably, a line 52a of a predetermined pitch is formed in an inner surface of the hollow 52 so that the moving steam may be rotated. The screw line 52a is a concave line continuously formed in the inner surface of the hollow 52 into a predetermined depth.

More preferably, a diffusion means 59 is installed to the front of the inflow hole 54 so as to diffuse steam closely to the inner surface of the hollow 52. The diffusion means 59 may adopt a hemispherical member 59 as shown in FIG. 7. That is to say, an inflow steam is collided with the hemispherical member 59 and thus diffused toward the inner surface of the hollow 52, and the steam diffused toward the inner surface is rotated by the screw line 52a. If the steam is rotated as mentioned above, the rotating means 55 may be rotated more effectively.

The rotating means 55 is rotated by steam to rotate the nozzle unit 60.

Figure 8:
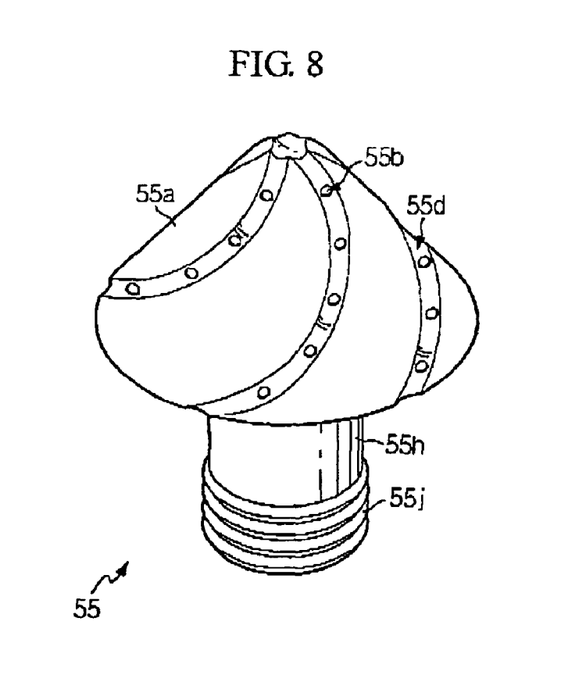
FIG. 8 is a perspective view showing a rotating means of the sterilizing apparatus of FIG. 5.

The rotating means 55 includes a rotator 55a having a cylindrical shape, and a rotary shaft 55h integrally formed with the rotator 55a and coupled with the nozzle unit 60.

The rotator 55a has a first inflow hole 55b formed in its outer circumference, and first through holes 55c communicated with the first inflow hole 55b and formed in a length direction of the rotator 55a.

The first inflow holes 55b are formed on the outer circumference of the rotator 55a at regular intervals. The steam rotates the rotator 55a with being introduced into the first through hole 55c through the first inflow holes 55b.

As shown in FIG. 8, a concave groove line 55d for interconnecting the first inflow holes 55b is preferably formed in the outer circumference into a predetermined depth. The concave groove line 55d is continuously formed with a predetermined curvature so that the rotator 55a may be rotated by steam. That is to say, after the steam is moved to the outer circumference of the rotator 55a, it flows along the concave groove line 55d, thereby rotating the rotator 55a.

As mentioned above, the steam rotates the rotator 55a with flowing along the concave groove line 55d, and also it rotates the rotator 55a with flowing into the first through hole 55c through the first inflow holes 55b.

The rotary shaft 55h includes a second through hole 55i communicated with the first through hole 55c, and a screw 55j for coupling with the nozzle unit 60.

The second through hole 55i is communicated with the first through hole 55c so that the steam moved through the first inflow holes 55b and the first through hole 55c is discharged to the nozzle unit 60. A screw thread is formed on an outer circumference of the screw 55j for coupling with the nozzle unit 60.

The nozzle unit 60 includes a rod-shaped nozzle 62, and a coupling unit for coupling with the screw 55j. An injection hole 62 for injecting steam is formed in the nozzle 62. Though it is illustrated in the drawings that the injection hole 63 are formed in a die at predetermined intervals, the injection holes 63 may be formed in various ways, not limited to the above. That is to say, the injection hole 63 may be formed in a front side of the nozzle 62.

Preferably, the nozzle 62 is elongated in a length direction so as to inject steam with being inserted into a passage of cold or warm water of the water dispenser 10, a passage of purified water of the water purifier 10a, the discharge pipe 27 of the beverage bending machine 20, and the air suction unit 32 of the air conditioner. The passage of cold or ward water of the water dispenser 10, the passage of purified water of the water purifier 10a, the discharge pipe 27 of the beverage bending machine 20, and the air suction unit 32 of the air conditioner are already explained above.

Figure 9:
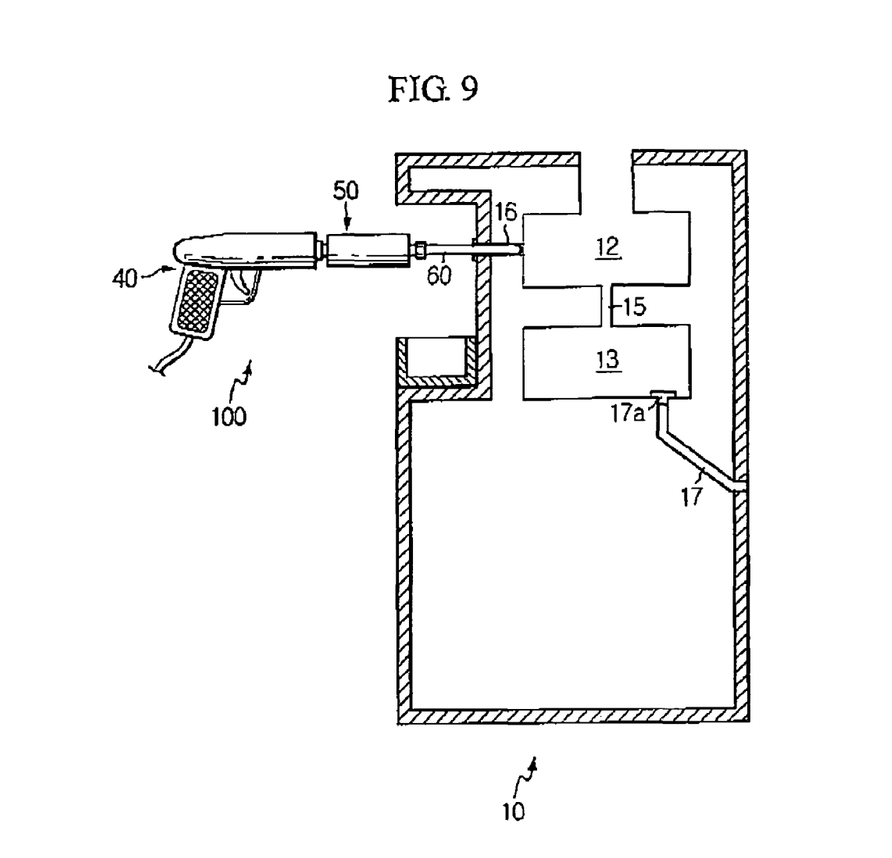
FIG. 9 is a sectional view illustrating that an outlet pipe of a water purifier is sterilized using the sterilizing apparatus of FIG. 5.

After the cold water valve 14 of the water dispenser 10 is removed, as shown in FIG. 9, the nozzle 62 is inserted into the cold water pipe 16 to inject steam thereto and thus sterilize the inside of the cold water pipe 16. The passage of purified water of the water purifier and the discharge pipe 27 of the beverage bending machine 20 may also be sterilized in the same way.

In addition, in case the air suction unit 32 of the air conditioner 30 is sterilized, the suction louver 33 is removed, and then the nozzle 62 is inserted among the evaporation pipe 32d and inject a steam thereto, or injects a steam toward the filters 32b, 32c.

Figure 10:
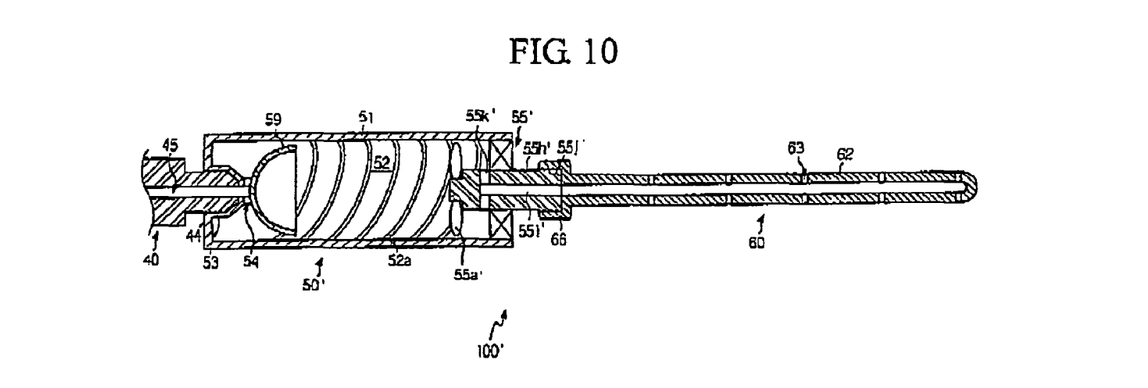
FIG. 10 is a sectional view showing a rotating unit and a nozzle unit of a sterilizing apparatus using a high pressure steam according to another embodiment of the present invention.

FIG. 10 is a sectional view showing a rotating unit and a nozzle unit of a sterilizing apparatus using a high pressure steam according to another embodiment of the present invention. In FIG. 10, the same reference numeral as in FIG. 7 designates the same component as in FIG. 7 having the same function.

The sterilizing apparatus 100' includes an injection member 40 for injecting a high pressure steam, a rotating unit 50' having a rotating means 55' rotated by the steam injected from the injection member 40, and a nozzle unit 60 connected to the rotating means 55' to inject a steam with rotating together with the rotating means 55'.

The injection member 40 and the nozzle unit 60 are identical to those of the former sterilizing apparatus 100, and not described in detail here.

The rotating means 55' includes a rotating shaft 55h' coupled with the nozzle unit 60, and a propeller 55a' installed to the rotating shaft 55h' and rotated by steam.

The rotating shaft 55h' includes a second inflow hole 55k' formed in a side for inflow of steam, a third through hole 55i' formed in a length direction and communicated with the second inflow hole 55k', and a screw 55j' formed at an end for coupling with the nozzle unit 60.

The propeller 55a' is introduced through the inflow hole 54 and rotated by the steam diffused by the diffusion means 59. The rotating force of the propeller 55a' is transferred to the nozzle unit 60 through the rotating shaft 55h'.

Figure 11:
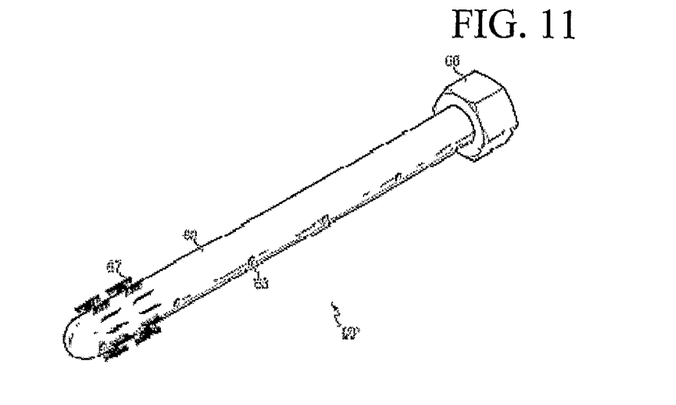
FIG. 11 is a perspective view showing a nozzle unit applicable to the sterilizing apparatus of FIG. 5 or 10.

FIG. 11 is a perspective view showing a nozzle unit applicable to the sterilizing apparatus of FIG. 5 or 10. The nozzle unit 60' includes a rod-shaped nozzle 62, a coupling unit 66 for coupling with the screw 55j, 55j', and brush members 67 installed to the nozzle 62. The nozzle 62 and the coupling unit 66 are identical to them of the former nozzle unit 60, and not described in detail here.

The brush members 67 are used for removing impurities in the water dispenser 10 or the water purifier 10a, impurities among the evaporation pipe 32d, impurities stuck to the filter 32b, 32c, when being inserted into the passage of cold and warm water of the water dispenser 10, the passage of purified water of the water purifier 10a, the discharge pipe 27 of the beverage bending machine 20, and the air suction unit 32 of the air conditioner 30. Though the brush members 67 are installed to a side of the nozzle 62 at regular intervals, the brush members 67 may be installed in various ways to various positions of the nozzle 62.

Figure 12:
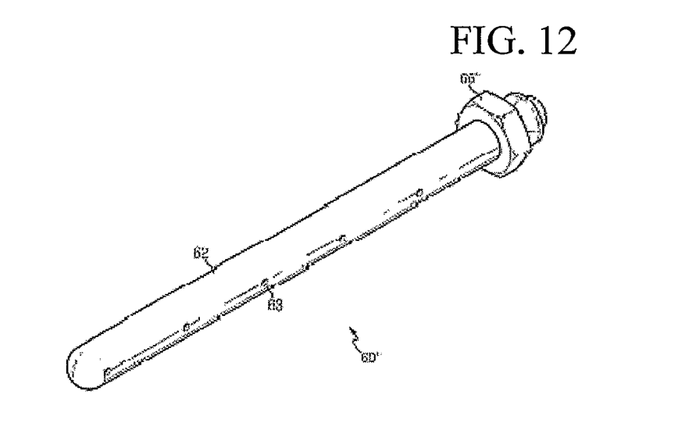
FIG. 12 is a perspective view showing a nozzle unit applicable to a sterilizing apparatus using a high pressure steam according to still another embodiment of the present invention.

FIG. 12 is a perspective view showing a nozzle unit applicable to a sterilizing apparatus using a high pressure steam according to still another embodiment of the present invention.

The nozzle unit 60" includes a rod-shaped nozzle 62, and a coupling unit 66" for coupling with the rotating means. The nozzle 62 is identical to that of the former nozzle unit 60, and not described in detail here.

The coupling unit 66" is fitted into the rotating means, namely using a coupler. This coupler is widely used for a shower, a sprayer, a hose connector and so on, and not described in detail here. Meanwhile, a brush member (not shown) may be further installed to the nozzle 62.

Figure 13:
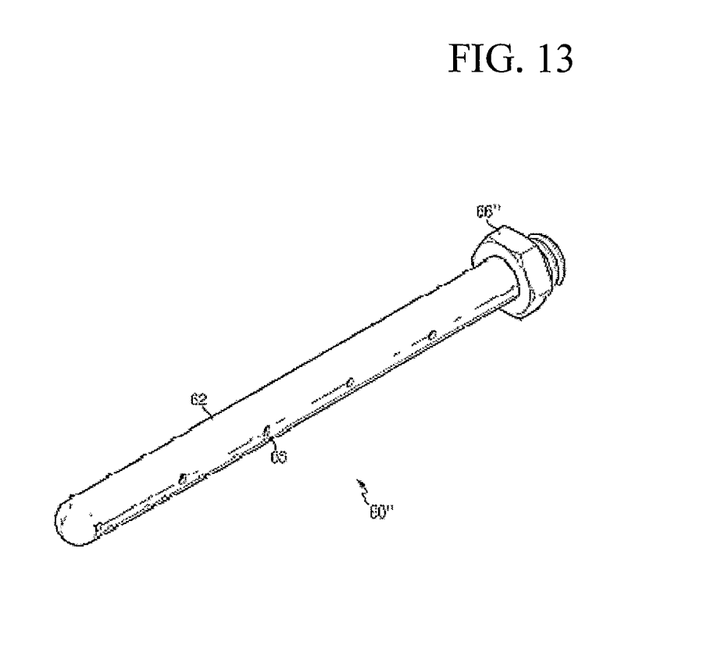
FIG. 13 is a perspective view showing a nozzle unit applicable to a sterilizing apparatus using a high pressure steam according to further another embodiment of the present invention.

FIG. 13 is a perspective view showing a nozzle unit applicable to a sterilizing apparatus using a high pressure steam according to further another embodiment of the present invention.

The nozzle unit 60''' includes a rod-shaped nozzle 62, and a coupling unit 66''' for coupling with the rotating means. The nozzle 62 is identical to that of the former nozzle unit 60, and not described in detail here.

The coupling unit 66''' has a male screw formed thereon. That is to say, the male screw is screwed to the rotating means having a female screw. Meanwhile, a brush member (not shown) may be further installed to the nozzle.

Meanwhile, though the nozzle 62 has been illustrated to have a rod shape, the nozzle may be bent at a predetermined angle, for example 45 degrees. In addition, the nozzle may also be formed to have a predetermined curvature. The nozzle bent at a predetermined angle or having a predetermined curvature is effective for sterilizing the evaporation pipe 32d of the air suction unit 32 of an air conditioner.

In addition, the nozzle may be made of a flexible material. The nozzle made of a flexible material may be used in case the cold water pipe 16, the warm water pipe, the connection pipe 15, the supply pipe 12a, or the discharge pipe 17, 27 is bent. In this case, the nozzle is preferably directly coupled to the screw thread 44 of the injection member 40. That is to say, it is preferred to inject steam without rotating the nozzle. It will be explained in more detail later.

Now, a method for sterilizing the passage of cold or warm water in the water dispenser 10 with the sterilizing apparatus using a high pressure steam according to a preferred embodiment of the present invention will be described. Meanwhile, a method for sterilizing the passage of purified water in a water purifier 10a, the discharge pipe 27 of the beverage bending machine 10, or the air suction unit 32 of the air conditioner 30 will be easily understood from the method for sterilizing the passage of cold or warm water in the water dispenser 10, and not described in detail here.

First, the cold water valve 14 is separated from the cold water pipe 16, and then a nozzle unit 60 suitable for the cold water pipe 16 is coupled to the rotary shaft 55h.

Subsequently, the nozzle unit 60 is inserted into the cold water pipe 16, and then the controller 46 of the injection member 40 is pulled to inject a steam.

The injected steam is introduced through the inflow hole 54, and then diffused by the diffusion means 56 to be closely adhered to the inner surface of the hollow 52. The steam diffused close to the inner surface of the hollow 52 is moved with rotating by the screw line 52a. The moving steam with rotation is moved through the first inflow hole 55b of the rotator 55a and the first and second through holes 55c, 55i, thereby rotating the rotator 55a.

The steam is discharged to the nozzle unit 60 through the first and second through holes 55c, 55i, and the nozzle unit 60 is rotated together with the rotator 55a. The nozzle unit 60 injects a steam through the injection hole 63 with rotating. At this time, the nozzle unit 60' having the brush members 67 may effectively remove impurities stuck to the inside of the cold water pipe 16. A method for sterilizing the warm water pipe and the discharge pipe 17 is identical to that for the cold water pipe 16.

Meanwhile, the cold water 12, the connection pipe 15 and the warm water container 13 may be sterilized in a way of inserting the nozzle 62 from an upper position of the cold water container 12 and then injecting a steam, Though it has been illustrated that the steam injected from the injection member 40 is moved to the nozzle unit 60 via the rotating unit 50, 50', the steam may also be directly moved from the injection member 40 to the nozzle unit 60 and then injected. That is to say, the nozzle unit 60 may be directly coupled to the screw thread 44 of the injection member 40 and then inject a steam. In this case, the nozzle unit 60 will not rotate.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

The sterilizing apparatus and method using a high pressure steam according to the present invention give the following effects.

First, this apparatus may be inserted into a passage of cold or warm water in a water dispenser, a passage of purified water in a water purifier, a discharge pipe of a beverage bending machine, an air suction unit of an air conditioner or the like and then inject a high pressure steam thereto for sterilizing.

Second, the apparatus and method is effective in removing impurities stuck to a passage of cold or warm water in a water dispenser, a passage of purified water in a water purifier, a discharge pipe of a beverage bending machine, an air suction unit of an air conditioner or the like.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. A sterilizing apparatus using a high pressure steam, comprising:
   an injection member for controlling the high pressure steam to be selectively injected;
   a nozzle unit having a rod-shaped nozzle for injecting the steam;
   a rotating unit having a hollow perforated in a length direction of the rotating unit so that the steam injected from the injection member passes through the hollow, a rotating means being installed in the hollow to be rotated by the passing steam, wherein:
   the nozzle unit injects the steam while being inserted in a subject to be sterilized, thereby sterilizing the subject,
   the nozzle unit is coupled to the rotating means to inject the steam while rotating together with the rotating means, and
   a screw line of a predetermined pitch is formed in an inner surface of the hollow so that the moving steam is rotated,
   wherein the rotating means includes:
      a cylindrical rotator having a first inflow hole formed in an outer surface thereof for introducing the steam, and a first through hole communicated with the first inflow hole and formed in a length direction thereof; and
      a rotary shaft integrally formed with the rotator and having a second through hole communicated with the first through hole and perforated in a length direction thereof, the rotary shaft being coupled with the nozzle unit,
   whereby the rotating means is rotated as the steam rotated by the screw line is introduced into the first inflow hole.

2. The sterilizing apparatus using a high pressure steam according to claim 1, further comprising a diffusion means installed in front of an inflow hole of the injection member; to diffuse the steam introduced from the injection member so that the steam is closely adhered to the inner surface of the hollow.

3. The sterilizing apparatus using a high pressure steam according to claim 1,
   wherein a brush member is installed to the nozzle.

4. The sterilizing apparatus using a high pressure steam according to claim 1,
   wherein the nozzle is elongated in a length direction so that the nozzle is injected into any of a passage of cold or warm water in a water dispenser, a passage of purified water in a water purifier, a discharge pipe of a beverage bending machine and an air suction unit of an air conditioner and then injects a steam with rotating.

* * * * *